(12) United States Patent
Fojtik

(10) Patent No.: US 7,041,084 B2
(45) Date of Patent: May 9, 2006

(54) HAND-HELD, HAND OPERATED POWER SYRINGE AND METHODS

(76) Inventor: Shawn P. Fojtik, 2080 Mahre Dr., Park City, UT (US) 84098

( * ) Notice: Subject to any disclaimer, the term of this patent is extended or adjusted under 35 U.S.C. 154(b) by 0 days.

(21) Appl. No.: 09/864,967

(22) Filed: May 24, 2001

(65) Prior Publication Data

US 2004/0116873 A1 Jun. 17, 2004

(51) Int. Cl.
*A61M 5/00* (2006.01)

(52) U.S. Cl. .................. 604/181; 604/218; 604/224; 604/233

(58) Field of Classification Search .............. 604/181, 604/218, 187, 232–235, 223, 227, 228, 61, 604/224, 246
See application file for complete search history.

(56) References Cited

U.S. PATENT DOCUMENTS

| | | | |
|---|---|---|---|
| 4,067,334 A | 1/1978 | Haller | |
| 4,364,388 A | 12/1982 | Cech | |
| 4,581,021 A | 4/1986 | Landau et al. | |
| 4,632,669 A | 12/1986 | Phipps, Sr. et al. | |
| 4,715,378 A * | 12/1987 | Pope, Jr. et al. | 128/344 |
| 4,737,151 A | 4/1988 | Clement et al. | |
| 4,832,692 A | 5/1989 | Box et al. | |
| 5,304,147 A | 4/1994 | Johnson et al. | |
| 5,306,147 A | 4/1994 | Dragan et al. | |
| 5,330,074 A | 7/1994 | Wirsig et al. | |
| 5,332,122 A | 7/1994 | Herold et al. | |
| 5,336,201 A * | 8/1994 | von der Decken | 604/223 |
| 5,439,131 A | 8/1995 | Kato | |
| 5,507,727 A | 4/1996 | Crainich | |
| 5,511,556 A | 4/1996 | DeSantis | |
| 5,514,071 A | 5/1996 | Sielaff, Jr. et al. | |
| 5,560,373 A | 10/1996 | De Santis | |
| 5,569,208 A | 10/1996 | Woelpper et al. | |
| 5,733,258 A * | 3/1998 | Lane | 604/51 |
| 5,951,517 A | 9/1999 | Lampropoulos et al. | |
| 5,968,017 A | 10/1999 | Lampropoulos et al. | |
| 6,004,295 A * | 12/1999 | Langer et al. | 604/164 |
| 6,024,728 A | 2/2000 | Schulz | |
| 6,030,368 A * | 2/2000 | Anwar et al. | 604/223 |
| 6,059,759 A | 5/2000 | Mottola et al. | |

OTHER PUBLICATIONS

21 C.F.R. § 870.1200, 1 pg.
21 C.F.R. § 870.1300, 1 pg.
21 C.F.R. § 870.1650, 1 pg.
21 C.F.R. § 880.5570, 1 pg.
21 C.F.R. § 880.5860, 1 pg.
BD Products, BD (Becton Dickinson and Company) Product Information, 2003, 2 pgs.
Merit Medical Products, Merit Medical Products Information, 2002, 8 total pgs.

* cited by examiner

*Primary Examiner*—Long V. Le
*Assistant Examiner*—Ann Y. Lam
(74) *Attorney, Agent, or Firm*—TraskBritt, PC

(57) ABSTRACT

A hand-held power syringe. The power syringe includes a handle with pivotally connected first and second members. The first member is also pivotally connectable to a syringe barrel, while the second member is pivotally connectable to a syringe plunger. These three pivotal connections provide leverage for forcing high viscosity fluids into and out of a receptacle of the syringe barrel. One or both of the first and second members of the handle may be bent to facilitate a user's gripping and movement of the first and second handle members. The power syringe may be used in any suitable injection, infusion, or sample-obtaining application, including angiography and angioplasty.

19 Claims, 5 Drawing Sheets

HAND-HELD, HAND OPERATED POWER SYRINGE AND METHODS

BACKGROUND OF THE INVENTION

1. Field of the Invention

The present invention relates generally to apparatus for facilitating the movement of a plunger of a syringe through a barrel of the syringe and, more particularly, to hand-held, hand operated apparatus that facilitate the movement of a plunger through a syringe barrel. More specifically, the present invention relates to hand-held apparatus with scissor grip type leveraged triggering systems that force a plunger of a syringe through the length of the barrel of the syringe.

2. Background of Related Art

Apparatus that facilitate the ejection of fluids from syringes are well known. Such apparatus are often referred to as fluid delivery devices or power syringes.

Conventionally, fluid delivery devices have been used to inject liquids, such as contrasting media (e.g., dyes, carbon dioxide, etc.) and medicines into patients. With many fluid delivery devices, the rate at which a fluid is injected into a patient's body may be controlled. While some of these devices are automated, others may be manually operated.

Due to the increase in delivery force provided by fluid delivery devices, such devices are particularly useful for injecting high viscosity fluids, which would otherwise be difficult, if not impossible, to inject by forcing one's thumb against the plunger of a conventional hand-held syringe.

Some hand-held power syringes, such as that disclosed in U.S. Pat. No. 5,330,074, issued to Wirsig et al. (hereinafter "the '074 Patent"), include ratcheting type mechanisms to assist a user in applying force to a plunger of the syringe. Ratcheting mechanisms are, however, often complex and, consequently, add to the manufacturing costs of such hand-held power syringes.

Other hand-held fluid delivery devices include handles with a fixed member and a movable member associated therewith. In one example of such a syringe, disclosed in U.S. Pat. No. 6,059,759, issued to Lampropoulos et al. (hereinafter "the '759 Patent"), the movable member may be slidingly secured to the fixed member. A plunger is forced into a syringe barrel as a user squeezes the handle members toward one another. Nonetheless, such a syringe only assists the user in forcing the plunger into the syringe barrel by transferring the location where force must be applied and increasing the area of a member to which force must be applied. Alternatively, the ends of the movable member and the fixed member of the handle may be pivotally secured to one another, as described in U.S. Pat. No. 6,024,728, issued to Schulz (hereinafter "the '728 Patent"). In either event, an upper end of the movable member either directly or indirectly engages a plunger of the syringe. Upon squeezing the two members of the handle, the movable member moves toward the fixed member and forces the plunger into the barrel of the syringe. Thus, the handle of such a syringe allows the force provided by a hand squeeze to be applied to the plunger of the syringe rather than the lesser amount of force that would otherwise be provided by use of a thumb to force the plunger into the syringe. Nonetheless, these fluid delivery devices may be difficult to use when the injection of high viscosity fluids is required, which may cause physical or mental discomfort to a patient into whom the fluid is being injected.

Some fluid delivery devices provide leverage to assist a user in forcing a plunger into or out of a syringe barrel. Examples of such devices are provided in U.S. Pat. No. 6,030,368, issued to Anwar et al. (hereinafter "the '368 Patent") and U.S. Pat. No. 4,737,151, issued to Clement et al. (hereinafter "the '151 Patent). The devices of the '368 and '151 Patents each include three pivot points to provide the desired amount of leverage: a first pivot point connecting a handle member to a plunger; a second pivot point connecting the handle member to a base member; and a third pivot point connecting the base member to a syringe barrel. While the base members of these devices are configured to be supported upon a table top or other flat surface, the generally straight handle members of these devices are configured to receive a downward force by a user, which is transferred to the plunger. As a user need only grip and move the handle member of such a device to move the plunger, the user can apply more force to the handle than that provided by a squeeze of the hand. Nonetheless, due to the manner in which the increased amount of force is applied, it is difficult for a user to make fine adjustments when injecting fluid into a body or extracting fluid therefrom.

Accordingly, there is a need for a fluid delivery apparatus that converts a small amount of controllable force, such as that provided by a squeeze of a hand, to a syringe plunger to faciliate movement of the plunger through a syringe barrel.

SUMMARY OF THE INVENTION

A fluid delivery apparatus incorporating teachings of the present invention is a hand-held type power syringe which includes a handle that is leveraged in such a manner as to apply an increased amount of pressure to the plunger of the syringe. The fluid delivery apparatus of the present invention may also include a syringe barrel with a fluid receptacle formed therethrough, as well as a plunger that inserts into a large end of the receptacle and that may be moved through at least a portion of the length of the receptacle.

The handle of the fluid delivery apparatus resembles a scissors and includes two members, a first of which is configured to be held by the fingers of an individual and the second of which is configured to be held by the individual's thumb or positioned against the palm of the individual. One or both of the first and second handle members may be bent so as to enable a user to grip both members with one hand while maximizing the amount of leverage provided as the handle members are forced toward one another.

A first pivot point of the handle pivotally connects the two members to one another at substantially central locations along the lengths thereof. When the first and second members of the handle are moved toward or away from one another, the first pivot point may remain in a substantially fixed position along the lengths of both the first and second members. Alternatively, the first pivot point may move in an elongate path relative to one or both of the first and second members of the handle as the positions of the first and second members are changed relative to one another. By way of example only, the first pivot point may move either eccentrically or in a linear fashion relative to one of the handle members as the positions of the members change while remaining substantially stationary relative to the other handle member.

A second pivot point of the handle may be associated with the syringe barrel such that the second pivot point itself remains relatively stationary to the syringe barrel as the fluid delivery device is being used. The second member of the handle is either directly or indirectly connected to the syringe barrel at the second pivot point.

The first member of the handle is connected, either directly or indirectly, to the plunger of the syringe at a third pivot point. Upon movement of the plunger into or out of the receptacle of the syringe barrel, the third pivot point remains substantially stationary relative to the plunger.

In both reusable and single-use embodiments of the fluid delivery apparatus of the present invention, the second member of the handle may be connected directly to an integral syringe barrel at the second pivot point, while the first member of the handle may be connected directly to an integral plunger at the first pivot point.

An alternative embodiment of the fluid delivery apparatus of the present invention is configured to receive a conventional, disposable syringe. In such an embodiment, the second member of the handle may be connected at the second pivot point to a syringe barrel retaining element which, in turn, receives the barrel of the disposable syringe. The first member of the handle may be connected at the third pivot point to a plunger-retaining element which, in turn, engages a portion of the plunger of the disposable syringe.

As an example of the use of a fluid delivery apparatus incorporating teachings of the present invention, a fluid to be injected into a patient may be drawn into the receptacle of the syringe barrel by moving the first and second members away from one another. Air may then be removed from a catheter or needle (e.g., a hypodermic needle or biopsy needle) that communicates with an end of the receptacle by squeezing the first and second members of the handle toward one another and the consequent movement of the plunger partially into the receptacle of the syringe barrel. If a catheter is coupled to the syringe, the catheter may be introduced into the patient or coupled with a catheter that has already been introduced into the patient. The fluid may then be injected into the patient through the needle or one or more catheters by further squeezing of the first and second handle members, which results in the plunger being moved further into the receptacle of the syringe barrel and displacement of fluid located in the receptacle and the catheter.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which illustrate exemplary embodiments of fluid delivery apparatus incorporating teachings of the present invention and features thereof.

DETAILED DESCRIPTION OF THE INVENTION

Figure 1:
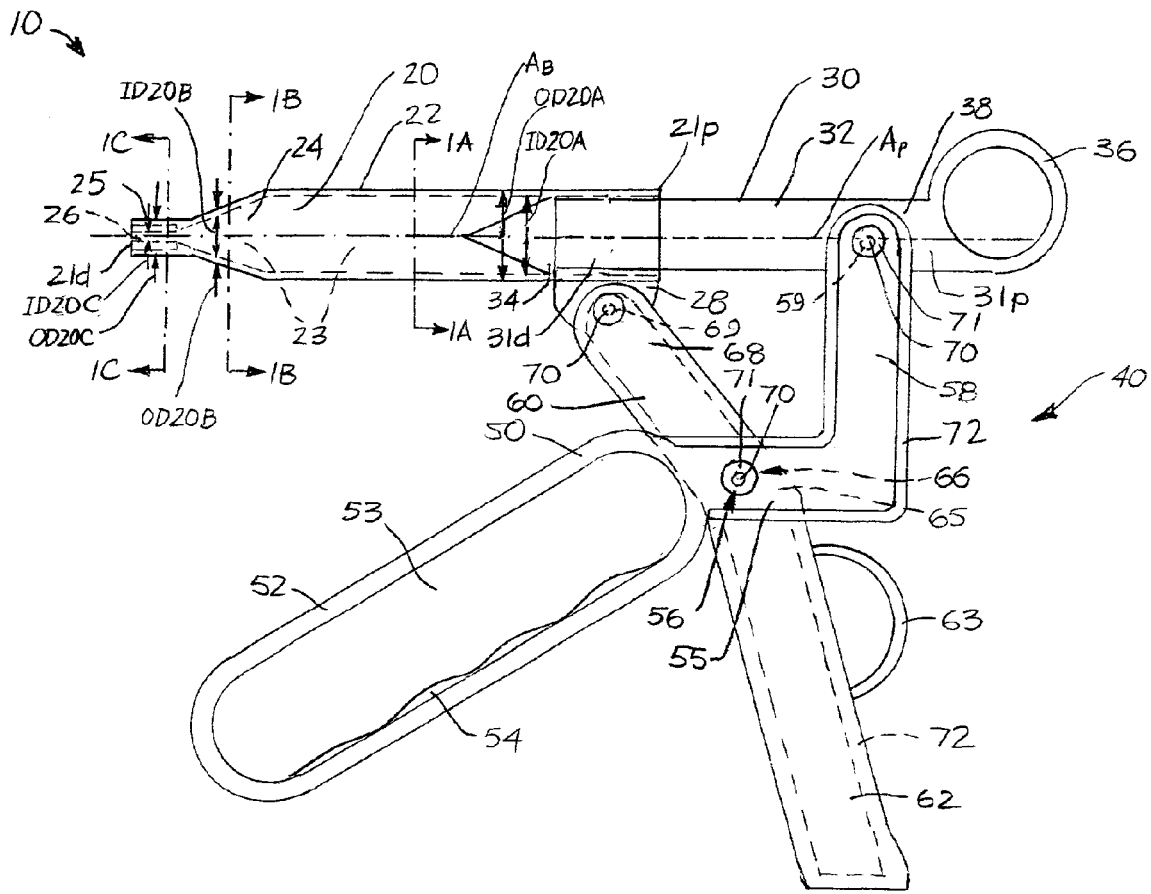
FIG. 1 is a side view of a power syringe incorporating teachings of the present invention, including a syringe barrel, a plunger that is longitudinally movable within a receptacle of the syringe barrel, and a scissor-grip handle that includes two members with three pivotal connection points, a first between a first member of the handle and the syringe barrel, a second between the second member of the handle and the plunger, and a third between the two handle members.

FIG. 1 illustrates an exemplary embodiment of a fluid delivery apparatus, or power syringe 10, incorporating teachings of the present invention. Power syringe 10 includes a barrel 20, a plunger 30 associated with barrel 20, and a scissor-grip handle 40 which causes plunger 30 to move longitudinally relative to barrel 20. One or both of barrel 20 and plunger 30 may be removable from handle 40 to facilitate the replacement of these elements and the reuse of handle 40.

Barrel 20 of power syringe 10 is an elongate member with a hollow interior extending through the length thereof. Along the majority of its length, barrel 20 is substantially uniform in both cross-sectional shape and cross-sectional dimensions. The region of barrel 20 having such substantial cross-sectional uniformity is referred to herein as body 22. As depicted, body 22 extends from a proximal end 21p of barrel 20 to a tapered section or region 24 thereof. A syringe tip 25 is located on the opposite side of tapered section 24, at the distal end 21d of barrel 20.

Figure 1A:
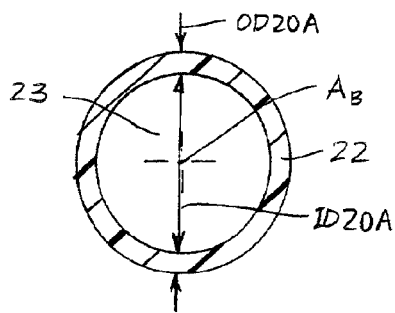
FIGS. 1A–1C are cross-sections taken along lines 1A—1A, 1B—1B, and 1C—1C, respectively, of FIG. 1.
Figure 1B:
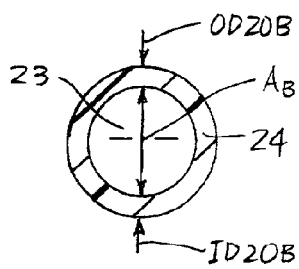
Figure 1C:
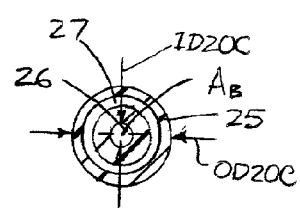

As shown in FIGS. 1–1C, the distances across opposed points of various cross-sections taken transverse to longitudinal axis $A_B$ of barrel 20 on the outer surface of barrel 20 or the outer diameter of barrel 20 are collectively referred to herein as OD20. The corresponding distances across opposed points of various cross-sections taken transverse to longitudinal axis $A_B$ on the inner surface of barrel 20 or the inner diameter of barrel 20 are collectively referred to herein as ID20.

As is depicted in FIGS. 1 and 1A, both OD20A and ID20A remain substantially the same along the substantial length of a body 22 of barrel 20. At tapered region 24, OD20 and ID20, which are respectively depicted at one location along the length of tapered region 24 as OD20B and ID20B, gradually (either linearly or along a curve) decrease from the sizes of OD20A and ID20A of body 22 to the much smaller sizes OD20C and ID20C of syringe tip 25. At syringe tip 25, the sizes of OD20C and ID20C are again substantially constant.

It is preferred that the taper of tapered region 24 occur at an angle of about 15° to longitudinal axis $A_B$ of barrel 20.

Other taper angles are, however, also within the scope of the present invention.

Figure 2:
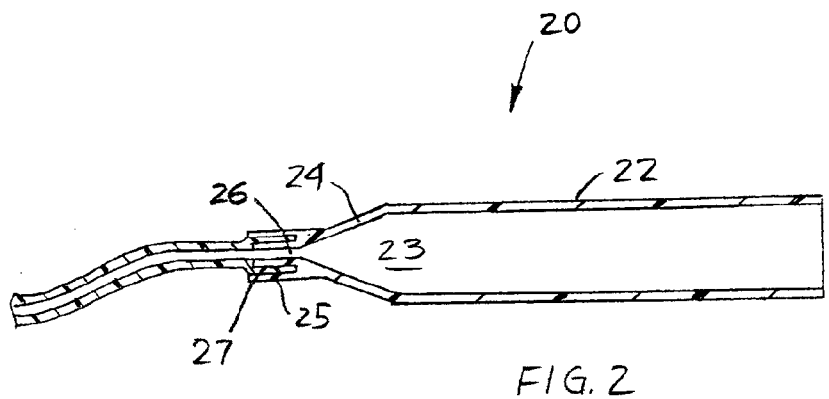
FIG. 2 is a cross-sectional representation of the syringe barrel of the power syringe of FIG. 1, illustrating the syringe barrel in an assembled relationship with a catheter.

Turning now to FIG. 2, within body 22 and tapered region 24 of barrel 20, the hollow interior thereof forms a receptacle 23. The volume of receptacle 23 is preferably suitable for the desired use of power syringe 10 (FIG. 1). For example, in applications where only small volumes of materials will be injected or aspirated with power syringe 10, barrel 20 may include a receptacle 23 with a relative small volume (e.g., 5 cubic centimeters ("cc"), 10 cc, etc.). When power syringe 10 is to be used to inject or aspirate larger volumes of materials, the volume of receptacle 23 may also be larger (e.g., 20 cc, 30 cc, 60 cc, etc.). Alternatively, receptacle 23 of barrel 20 may have other standard syringe volumes or a volume that is tailored to a specific use for power syringe 10.

The hollow interior of syringe tip 25 is referred to herein as a lumen 26. Lumen 26 may have a diameter of as small as about 1 mm (0.40 inch) or smaller. Of course, syringe tips 25 with different sizes of lumens 26 are within the scope of the present invention, as the size of a lumen 26 depends at least partially upon the gauge of a needle or the lumen size of a catheter to be coupled with syringe tip 25.

In addition, in order to facilitate the coupling of a needle or catheter with syringe tip 25, syringe tip 25 includes a coupling member 27 at or near the distal end 21d of barrel 20. Although FIG. 1 depicts coupling member 27 as including a cylindrically shaped recess that extends partially into syringe tip 25, coupling members of other configurations, including, without limitation, threaded or nonthreaded coupling members that facilitate the coupling of a needle, catheter, or other member to an outer surface of syringe tip 25, are also within the scope of the present invention.

Figure 3:
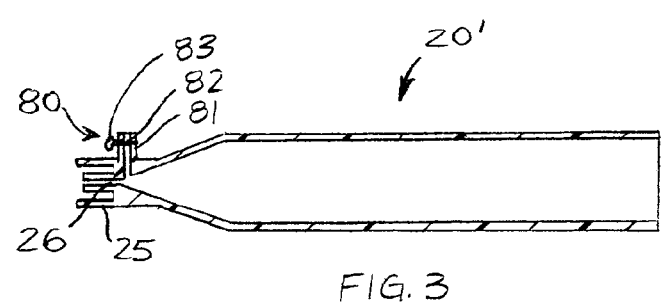
FIG. 3 is a cross-sectional representation of a variation of the syringe barrel illustrated in FIGS. 1 and 2, which includes an aspiration port that may communicate with a source or reservoir for introducing fluid into the syringe barrel upon appropriate movement of the plunger to increase the available volume within the syringe barrel.

As illustrated in FIG. 3, a variation of barrel 20' may include an aspiration port 80 proximate syringe tip 25. Aspiration port 80 facilitates the introduction of a fluid, such as a saline solution, medicine, anesthetic, indicator solution (e.g., dye, radioactive solution, radioopaque solution or x-ray contrast media, etc.), other chemical compound, or the like from an external source into receptacle 23 of barrel 20. Aspiration port 80 is depicted as comprising a cylindrical protrusion 81, which is configured to have a length of tubing coupled thereto, and a lumen 82 that extends through protrusion 81 and communicates with lumen 26 of syringe tip 25. In addition, aspiration port 80 may include a valve 83, such as a stop cock type valve, which opens and closes lumen 82. Of course, other configurations of aspiration ports are also within the scope of the present invention.

Referring again to FIG. 1, barrel 20 also includes a handle connection element 28. As depicted, handle connection element 28 extends from body 22 at proximal end 21p of barrel 20 and includes an aperture formed therethrough. The aperture is sized and configured to receive a hinge element 70 and, thus, to facilitate the connection of a member of handle 40 to barrel 20.

While FIG. 1 depicts barrel 20, receptacle 23, and lumen 26 as having substantially cylindrical shapes with circular cross-sections taken transverse to a longitudinal axis $A_B$ of barrel 20, syringe barrels with any other suitable cross-sectional shapes (e.g., ovals, ellipses, polygons, etc.) are also within the scope of the present invention.

With continued reference to FIG. 1, plunger 30 is an elongate member with dimensions that permit plunger 30 to be inserted into receptacle 23 of barrel 20 through proximal end 21p thereof. Plunger 30 includes a body 32 and a head 34 at the distal end 31d of body 32. The proximal end 31p of body 32 and, thus, of plunger 30 is configured to have force applied thereto to facilitate movement of plunger 30 in both directions along a longitudinal axis $A_P$ of plunger 30.

Head 34 of plunger 30 preferably comprises a somewhat deformable, resilient member. By way of example, head 34 may be formed from silicone or any other resilient polymer (i.e., rubber) that is suitable for use in medical applications. The shape of head 34 is preferably substantially complementary to a shape of the portion of receptacle 23 of barrel 20 that is located within tapered region 24 and a portion of body 22 adjacent thereto. The size of head 34 is preferably substantially the same as or somewhat larger than the correspondingly shaped portion of receptacle 23 so as to facilitate the substantial displacement of fluid from receptacle 23 as plunger 30 is fully inserted therein.

Preferably, in order to facilitate movement of head 34 of plunger 30 along the full length of receptacle 23, the length of plunger 30 is greater than the combined lengths of body 22 and tapered region 24 of barrel 20. Of course, in order to apply the amount of force necessary to move plunger 30 through the length of receptacle 23, body 32 of plunger 30 is preferably formed from a more rigid material than that of head 34. Accordingly, head 34 preferably includes a receptacle (not shown) that is configured to receive a corresponding head connection protrusion (not shown) at the distal end of body 32, as known in the art.

Proximal end 31p of plunger 30 includes a handle connection element 38. Handle connection element 38 includes an aperture formed through body 32 of plunger 30 at a location that facilitates the pivotal connection of a member of handle 40 thereto by way of a hinge element 70.

In addition, proximal end 31p of plunger 30 may include a secondary movement element 36, such as a loop or another member by which an individual may cause plunger 30 to move in one or both directions along longitudinal axis $A_P$ thereof.

Still referring to FIG. 1, handle 40 includes two elongate members, a first member 50 and a second member 60. First member 50 and second member 60 are pivotally connected with one another in a manner that, along with the shapes of first and second members 50 and 60, provides leverage so as to decrease the amount of force that must be exerted by and individual's hand to move plunger 30 relative to barrel 20.

First member 50, which is configured to be held with an individual's fingers, includes a gripping end 52 and a plunger attachment end 58. In addition, first member 50 includes pivotal connection element 56 positioned at a central region 55 thereof, which is located substantially centrally along the length thereof, to facilitate connection of first member 50 to second member 60 of handle 40. Pivotal connection element 56 includes an aperture that has a circular shape and that receives a hinge element 70, or pivot pin, which, in turn, connects first member 50 and second member 60 to one another.

As shown, first member 50 includes an elongated loop 53 along gripping end 52, through which an individual's fingers may be inserted. Alternatively, or in addition to loop 53, gripping end 52 may include a finger grip 54 that is contoured so as to comfortably receive the fingers of an individual.

Plunger attachment end 58 includes a plunger connection element 59 that facilitates the pivotal connection of first member 50 to the corresponding handle connection element 38 of plunger 30. Plunger connection element 59 may comprise an aperture that is configured to receive hinge element 70. First member 50 and plunger 30 are pivotally connected to one another by positioning plunger attachment end 58 against the appropriate location of plunger 30 with plunger connection element 59 and aperture 39 of handle connection element 38 in alignment. A single hinge element 70 is then inserted through both plunger connection element 59 and aperture 39 of handle connection element 38. Hinge element 70 preferably includes an enlarged head 71 at each end thereof to maintain the assembled, pivotal relationship of plunger 30 and first member 50. Of course, other known types of pivotal connection arrangements between plunger 30 and first member 50 and their corresponding elements are also within the scope of the present invention.

First member 50 is bent, or angled, at some point along the length thereof, between gripping end 52 and plunger attachment end 58, to at least partially provide the desired amount of leverage for forcing plunger 30 to move longitudinally through receptacle 23 of barrel 20. As shown in FIG. 1, first member 50 is angled at two locations, a first of which is located between gripping end 52 and central region 55 and a second of which is located between central region 55 and plunger attachment end 58. Although FIG. 1 depicts gripping end 52 and central region 55 as being oriented at an angle of about 140° relative to one another and central region 55 and plunger attachment end 58 as being oriented at an angle of about 90° relative to one another, other angles and bend locations are also within the scope of the present invention.

Still referring to FIG. 1, second member 60 of handle 40 is an elongate member that is configured to be held by an individual's palm or thumb. Second member 60 includes a gripping end 62 and a barrel attachment end 68, as well as a central region 65 located between gripping end 62 and barrel attachment end 68.

Gripping end 62 of first member 60 may include a thumb loop 63 through which the thumb of an individual using power syringe 10 may be inserted.

Central region 65 of second member 60 includes a pivotal connection element 66 that corresponds to pivotal connection element 56 of first member 50. Pivotal connection element 66 may comprise an aperture formed through central region 65 and configured to receive hinge element 70. Upon properly orienting first member 50 and second member 60 relative to one another in an assembled relationship thereof and aligning the aperture of first member 50 with the aperture of second member 60, hinge element 70 may be inserted through the apertures to pivotally connect first and second members 50 and 60 to one another. Hinge element 70 preferably includes an enlarged head 71 at each end thereof to maintain the assembled, pivotal relationship of first member 50 and second member 60.

Figure 4:
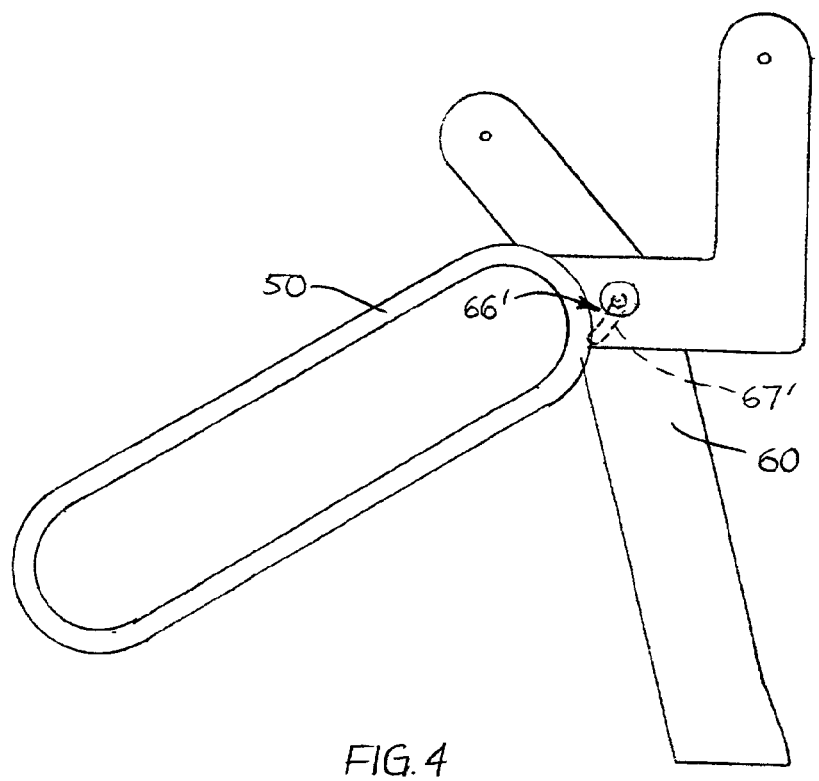
FIG. 4 is a side view that depicts a variation of the handle of FIG. 1, with one of the first and second members including an arcuate slot through which a movable connection member on the other of the two members moves when the handle members are moved relative to one another.

Alternatively, as depicted in FIG. 4, a variation of pivotal connection element 66' may comprise an arcuate slot 67', along the length of which pivotal connection element 56 may move as first and second members 50 and 60 are moved toward or apart from one another.

Figure 5:
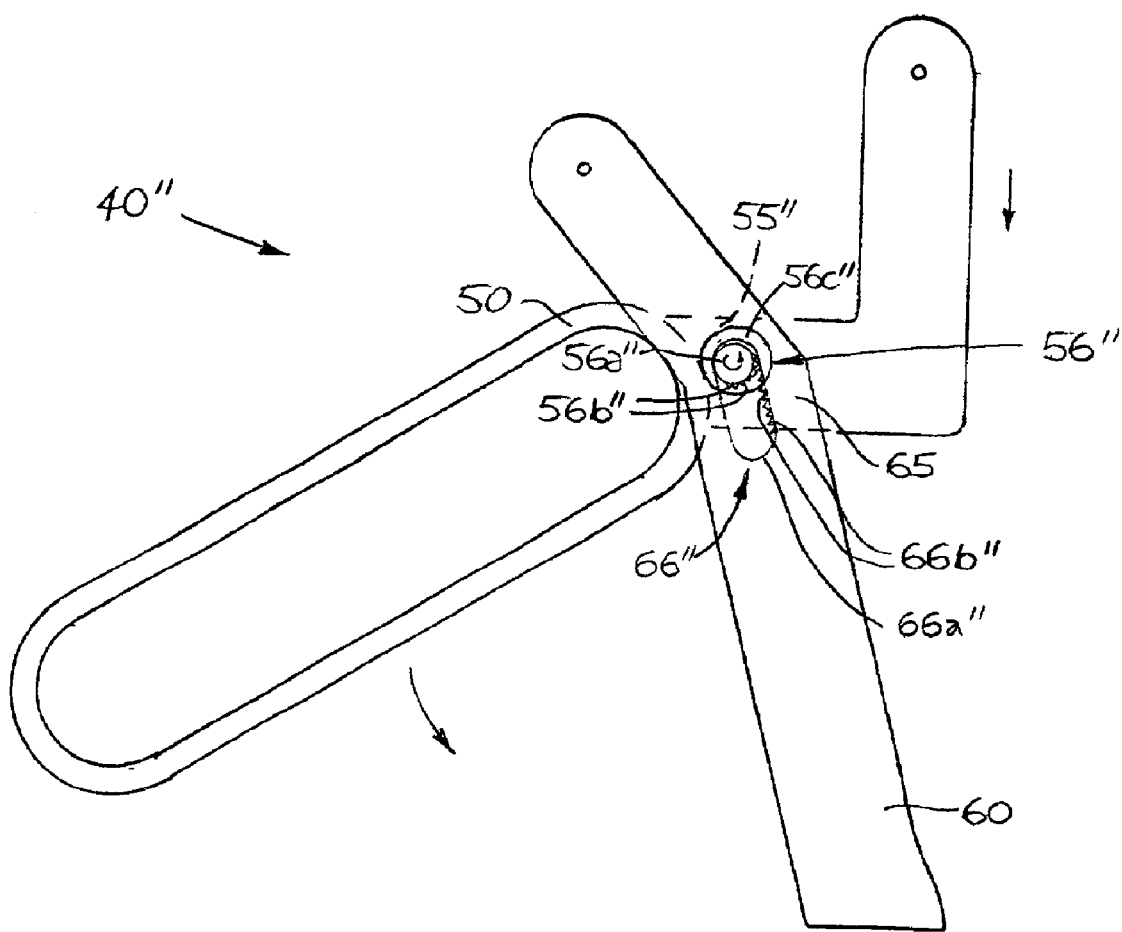
FIG. 5 is a side view that depicts another variation of the handle of FIG. 1, wherein one of the first and second handle members includes a partial gear member and the other of the first and second handle members includes an elongated slot with teeth along an edge thereof for receiving teeth of the partial gear member upon movement of the two handle members relative to one another.

As another alternative, shown in FIG. 5, a handle 40" of a power syringe according to the present invention includes another embodiment of connection element 56" on central region 55" of first member 50" and another, corresponding embodiment of pivotal connection element 66" on central region 65" of second member 60". Connection element 56", which protrudes from central region 55" and is fixed in relation thereto, includes a cylindrical section 56a", a series of adjacent teeth 56b" protruding from at least a portion of the curved surface of cylindrical section 56a", and an enlarged retention head 56c" adjacent cylindrical section 56a", opposite from the remainder of first member 50". The distance that cylindrical section 56a" protrudes from central region 55" of first member 50" is preferably slightly larger than the thickness of second member 60".

The corresponding pivotal connection element 66" of second member 60" comprises an elongated slot 66a" with a series of adjacent teeth 66b" protruding from at least a portion of an edge along the length of slot 66a". Teeth 66b" are configured and positioned complementarily to teeth 56b" of connection element 56" such that teeth 56b" and teeth 66b" cooperate by mutually engaging each other upon rotation of cylindrical section 56a" relative to slot 66a". The width of slot 66a" is preferably slightly larger than the diameter of cylindrical section 56a" of pivotal connection element 56" so as to substantially prevent side-to-side movement of pivotal connection element 56" relative to pivotal connection element 66". Consequently, the relative movement of pivotal connection elements 56" and 66" with respect to one another is substantially confined on the direction in which pivotal connection element 66" extends, which, as illustrated, is along the length of second handle 60". Thus, when first and second handle members 50" and 60" are forced toward one another, pivotal connection element 56" rotates relative to pivotal connection element 66" and moves downward through slot 66a" of pivotal connection element 66". Conversely, when first and second handle members 50" and 60" are forced apart from one another, pivotal connection element 56" rotates and moves in the opposite direction relative to pivotal connection element 66".

Referring again to FIG. 1, when first and second members 50 and 60, or variations thereof, have been properly assembled with one another, it is preferred that practically any adult user be able to properly position their fingers on gripping end 52 and their thumb or palm against gripping end 62 while gripping ends 52 and 62 are spaced a maximum distance apart from one another with head 34 of plunger located at proximal end 21p of barrel 20.

Barrel attachment end 68 includes a barrel connection element 69 that facilitates the pivotal connection of second member 60 to the corresponding handle connection element 28 of barrel 20. As depicted, barrel connection element 69 comprises an aperture that is configured to receive a hinge element 70. Second member 60 and barrel 20 are pivotally connected to one another by properly positioning barrel attachment end 68 and handle connection element 28 against one another, with the apertures thereof in alignment, and inserting a single hinge element 70 through both barrel connection element 69 and handle connection element 28. Hinge element 70 preferably includes an enlarged head 71 at each end thereof to maintain the assembled, pivotal relationship of barrel 20 and second member 60. Of course, other known types of pivotal connection arrangements between barrel 20 and second member 60 and their corresponding elements are also within the scope of the present invention.

Second member 60 of handle 40 may be bent, or angled, to increase the leverage provided by first member 50 and the scissor-like arrangement of first member 50 and second member 60. As illustrated, second member 60 is bent at central region 65 thereof to position gripping end 62 in proximity to gripping end 52 of first member 50 when first member 50 and second member 60 are in an appropriate assembled relationship.

Of course, one or both of first member 50 and second member 60 may include reinforcement ribs 72 or other reinforcement structures along at least a portion of the length thereof. As depicted, reinforcement ribs 72 are positioned along the edges of first member 50 and second member 60. Reinforcement ribs 72 may be positioned to prevent side-to-side bending of first member 50 or second member 60 during use of handle 40 to move plunger 30 relative to barrel 20.

Figure 6:
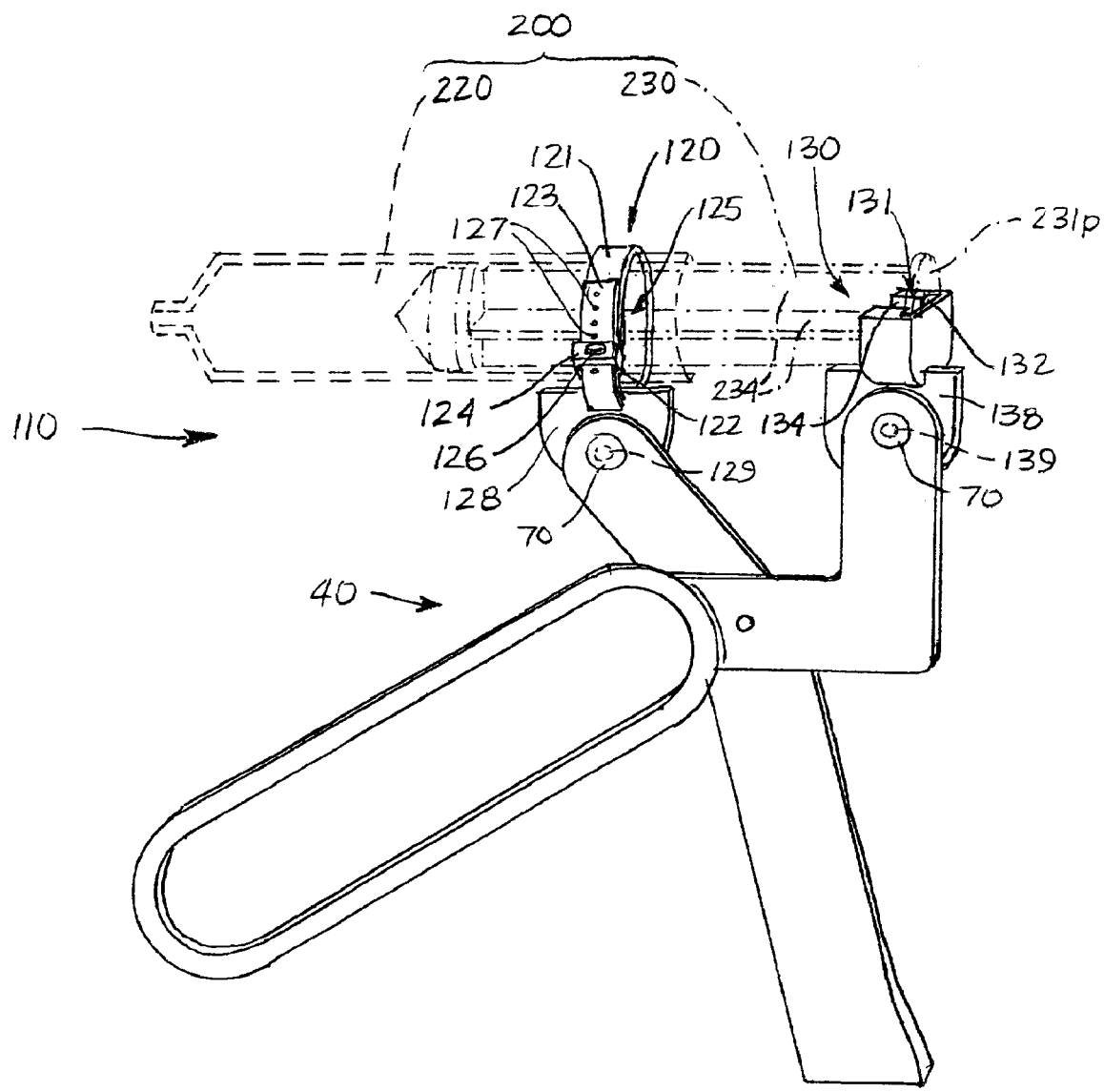
FIG. 6 is a side view of an alternative embodiment of a power syringe incorporating teachings of the present invention, wherein a disposable syringe barrel and plunger may be assembled and used with a reusable injection/aspiration handle.

Turning to FIG. 6, another embodiment of a power syringe 110 according to the present invention is illustrated. Power syringe 110 includes a scissor-grip handle 40, a barrel retaining member 120 pivotally secured to a second member 60 of handle 40, and a plunger biasing member 130 pivotally secured to a first member 50 of handle 40.

Barrel retaining member 120 is configured to engage and retain at least a portion of the barrel 220 of a syringe 200. The depicted, exemplary embodiment of barrel retaining member 120 includes a flexible, elongate member 121 with a receptacle 124 at one end 122 thereof. Receptacle 124 is configured to receive the other end 123 of elongate member 121, as well as to facilitate the movement of a received portion of elongate member 121 therethrough. When receiving end 123 of elongate member 121 has been inserted into or through receptacle 124, barrel retaining member 120 takes on an annular configuration, forming a barrel receptacle 125 that may receive a portion of barrel 220 of syringe 200. As elongate member 121 moves through receptacle 124, the size of barrel receptacle 125 changes. The position of a portion of elongate member 121 extending through receptacle 124 may be maintained by way of a size adjustment member 126 (e.g., a screw, a spring-biased pin, etc.) that protrudes into receptacle 124 to engage the portion of elongate member 121 therein. Elongate member 121 may also include retention recesses 127 (e.g., grooves, slots, etc.) that are oriented along the length of elongate member 121 and that are configured to receive an interior end of size adjustment member 126 so as to further maintain the position of elongate member 121 relative to receptacle 124 and, thus, the size of barrel receptacle 125.

Barrel retaining member 120 also includes a handle connection element 128 which extends from elongate member 121 and includes an aperture 129 therethrough. Aperture 129 is sized and configured to receive a hinge element 70 and, thus, to facilitate connection of a member of handle 40 to barrel retaining member 120.

Of course, other embodiments of barrel retaining members, which may be configured to receive a variety of different sizes of syringes or single syringe sizes, are also within the scope of the present invention.

With continued reference to FIG. 6, an exemplary embodiment of plunger biasing member 130 is configured to receive, retain, and apply force to a proximal end 231*p* of a plunger 230 of syringe 200. Accordingly, the illustrated plunger biasing retaining member 130 includes a plunger receiving portion 131 that is configured to receive and apply pressure to proximal end 231*p* of plunger 230. As illustrated, plunger receiving portion 131 includes a receptacle 132 that is configured to receive at least a portion of the disk-shaped proximal end 231*p* of a conventionally configured syringe plunger 230. In addition, plunger biasing retaining member 130 includes a slot 134 that is continuous with receptacle 132 and that is positioned and sized to receive a portion of at least one of the support ribs 234 of a conventionally configured syringe plunger 230. As depicted, proximal end 231*p* is substantially completely received within receptacle 132. Accordingly, slot 134 may include a narrow bottom section that receives a single, vertically oriented support rib 234 and a wider top section that receives opposed, horizontally oriented support ribs 234.

A handle connection element 138 is positioned adjacent to (beneath) plunger receiving portion 131 and includes an aperture 139 that is configured to receive a portion of a hinge element 70 and to pivotally connect plunger biasing member 130 to first member 50 of handle 40.

Handle 40 of power syringe 110 may be configured as described previously herein.

While the various elements of power syringe 10 may be manufactured from any suitable material or materials, it is preferred that each of the elements of power syringe 10 be formed by injection molding processes so as to afford low manufacturing cost and, consequently, to permit the disposal of at least barrel 20 and plunger 30 of power syringe 10 after use. For the more rigid elements of power syringe 10, which include substantially all of the elements thereof with the exception of head 34 of plunger 30, polycarbonates, such as LEXAN®, manufactured by General Electric, or MAKROLON®, manufactured by Miles Chemicals, may be used. Of course, other medical grade plastics having properties (strength, rigidity, structural integrity, ability to be adequately sterilized while maintaining other desired properties, etc.) that are suitable for the desired functions of the various elements of power syringe 10 may be used to form those elements. Alternatively, suitable metals, such as stainless steel, which have the desired properties may be used to form one or more of the elements of power syringe 10. However, these configurations are not requirements and the materials and method of fabrication are not critical to the invention.

Figure 7:
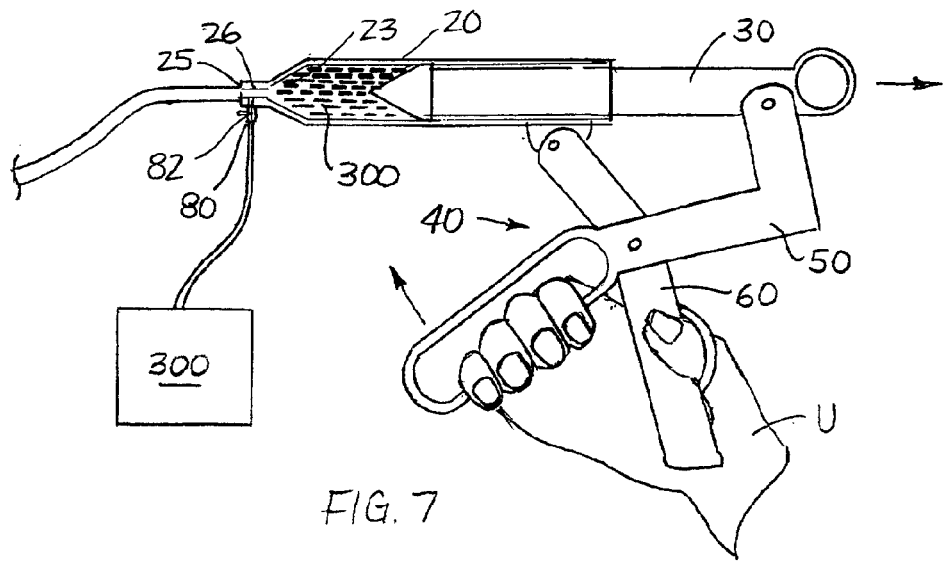
FIGS. 7–7B are schematic representations of use of a power catheter incorporating teachings of the present invention.
Figure 7A:
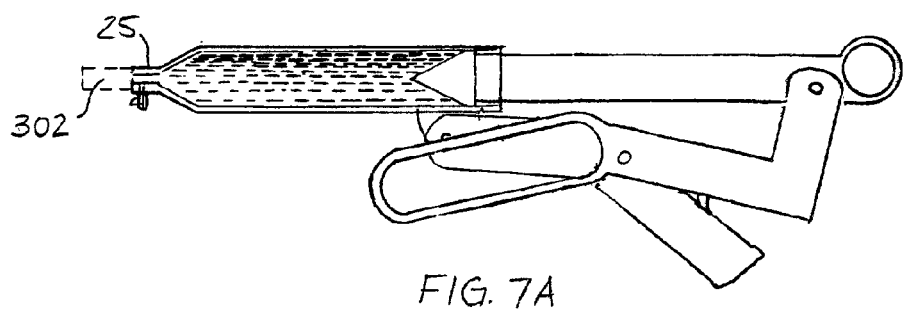
Figure 7B:
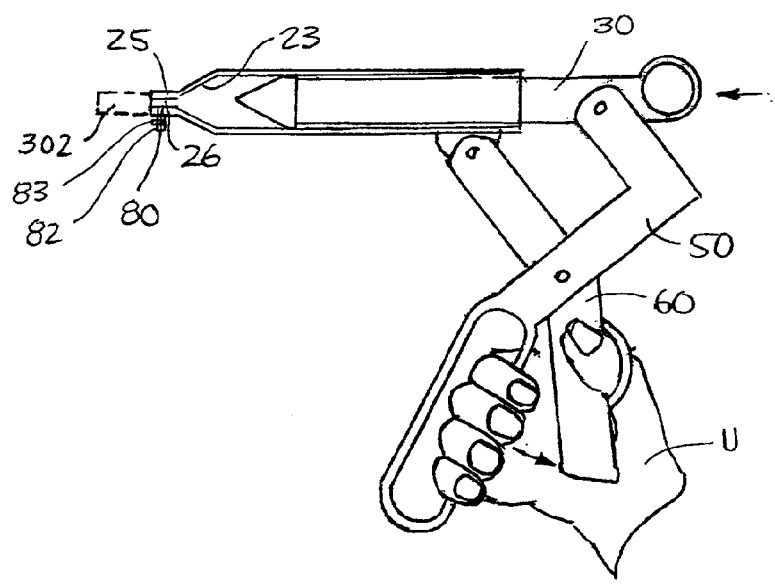

Turning now to FIGS. 7–7B, an example of the use of a power catheter incorporated teachings of the present invention is illustrated.

FIG. 7 illustrates the introduction of a fluid 300 into receptacle 23 of barrel 20 through either lumen 26 of syringe tip 25 (FIGS. 1 and 2) or lumen 82 of aspiration port 80 (FIG. 3) by drawing plunger 30 outwardly (proximally) through receptacle 23. Plunger 30 may be drawn outwardly through receptacle 23 by a user U forcing first and second members 50 and 60 of handle 40 apart from one another. As plunger 30 is drawn outwardly through receptacle 23, the available volume of receptacle 23 (i.e., that located distally relative to head 34 of plunger 30) increases and a negative pressure is created within receptacle 23. This negative pressure forces fluid 300 to enter receptacle 23. As depicted, fluid 300 is a liquid, such as a medicine, an anesthetic, a dye, or another chemical compound. Alternatively, fluid 300 may comprise a gas, air, or another mixture of gases.

As shown in FIG. 7A, syringe tip 25 may be coupled to a known infusion or injection apparatus 302, shown in phantom, such as a catheter or a hypodermic needle. Infusion or injection apparatus 302 comprises a conduit which facilitates the introduction of fluid 300 into the body of an individual.

In FIG. 7B, as user U forces first member 50 and second member 60 toward one another, plunger 30 is forced inwardly (i.e., distally) through receptacle 23, decreasing the available volume within receptacle 23 and creating an increase in pressure therein. This increase in pressure within receptacle 23 forces fluid 300 out of receptacle 23 through lumen 26 of syringe tip 25, through infusion or injection apparatus 302, and into the body of the individual. With valve 83 in a closed position or orientation, fluid 300 is prevented from escaping through lumen 82 of aspiration port 80 as the pressure within receptacle 23 is being increased.

The amount of fluid introduced into the individual's body may be controlled by controlling the distance first and second members 50 and 60 are forced together.

Returning reference to FIG. 1, the three-pivot-point configuration of handle 40 provides sufficient leverage that the force applied by a single hand of a user will be translated into an adequate amount of force upon plunger 30 and within receptacle 23 to force even relatively high viscosity fluids into and out of receptacle 23. Moreover, the configurations of members 50 and 60 of handle 40 facilitate gripping thereof with a single hand, the fine motor skills of which can be used in such a way as to precisely control the amount of fluid being introduced into or discharged from receptacle 23 of syringe barrel 20.

Power catheters incorporating teachings of the present invention may be used in a variety of different procedures, including, without limitation, injecting medicines or drugs into an individual, either through a hypodermic needle into the individual's tissues or intravenously (i.e., into a vein of an individual), introducing dyes or other indicator solutions into the bloodstream of a particular location of individual's body (e.g., in angiography), introducing a gas, air, or another gas mixture into an angioplasty balloon to inflate the same in a process which is typically referred to as percutaneous transluminal coronary angioplasty ("PTCA"), or obtaining samples of blood, other fluids, or tissues (e.g., with a biopsy needle or other biopsy instrument). A power syringe according to the present invention may also be used to remove air or gas from such a balloon or to obtain samples from the body of an individual, as well as in other applications where syringes have been used.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A power syringe, comprising:
   a syringe barrel including a receptacle for receiving fluid;
   a plunger insertable into said receptacle and moveable longitudinally therethrough; and
   a handle, including:
   a first member configured to be held by a first part of a user's hand, said first member being pivotally connected to said syringe barrel;
   a second member configured to be held by a second part of the user's hand, said second member being pivotally connected to said plunger; and
   a hinge connecting said first and second members to one another, at least one of said first and second members comprising a slot through which the hinge extends, said hinge and said slot including cooperating teeth.

2. The power syringe of claim 1, wherein said first member is pivotally connected to said syringe barrel by way of a barrel retaining member for releasably retaining said syringe barrel.

3. The power syringe of claim 1, wherein said second member is pivotally connected to said plunger by way of a plunger retaining member for releasably retaining said plunger.

4. The power syringe of claim 1, wherein said slot comprises an arcuate slot.

5. The power syringe of claim 1, wherein said teeth of said hinge and said teeth of said slot mutually engage each other to facilitate controlled movement of said hinge along a length of said slot.

6. The power syringe of claim 1, wherein at least one of said first and second members is configured to facilitate gripping thereof.

7. The power syringe of claim 6, wherein said at least one of said first and second members is angled.

8. A handle for a power syringe, comprising:
   a first member configured to be held with a first portion of a hand of a user and to be secured in pivotal relation to a syringe barrel;
   a second member configured to be held with a second portion of the same hand of the user and to be secured in pivotal relation to a syringe plunger, said first and second members being pivotally secured to one another, apertures formed through said first and second members; and
   a hinge that extends through said apertures to secure said first and second members in said pivotal relation, said hinge including teeth, and at least one of said apertures comprises a slot and teeth that cooperate with said teeth of said hinge.

9. The handle of claim 8, wherein said slot comprises an arcuate slot.

10. The handle of claim 8, wherein said teeth of said hinge and said teeth of said aperture mutually engage each other to facilitate controlled movement of said hinge along a length of said slot.

11. The handle of claim 8, further comprising a barrel retaining member pivotally secured to said first member.

12. The handle of claim 11, wherein said barrel retaining member is configured to releasably secure the syringe barrel.

13. The handle of claim 8, further comprising a plunger retaining member pivotally secured to said second member.

14. The handle of claim 13, wherein said plunger retaining member is configured to releasably secure the syringe plunger.

15. A method for introducing a fluid into a body, comprising: coupling one of an injection apparatus and an infusion apparatus to a syringe barrel; pivoting a first handle pivotally associated with said syringe barrel and a second handle pivotally associated with a syringe plunger away from one another to create a negative pressure within a receptacle of said syringe barrel to draw fluid into said receptacle with a single hand; and grasping said first handle and said second handle to pivot said first handle and said second handle toward one another to force said syringe plunger into said receptacle of said syringe barrel, wherein at least one of said first and second handle comprises a slot through which a hinge extends, said slot and said hinge including cooperating teeth, said first handle pivoting relative to said syringe barrel, said second handle pivoting relative to said syringe plunger, said syringe plunger displacing fluid within said receptacle to force the fluid through said injection apparatus or said infusion apparatus and into the body.

16. The method of claim 15, wherein the fluid comprises a medicine.

17. The method of claim 15, wherein the fluid comprises at least one gas.

18. The method of claim 17, wherein said coupling comprises coupling an angioplasty catheter that communicates with an angioplasty balloon to said syringe barrel.

19. The method of claim 15, wherein the fluid comprises an indicator solution.

* * * * *